(12) United States Patent
Jacobs et al.

(10) Patent No.: US 6,589,975 B2
(45) Date of Patent: *Jul. 8, 2003

(54) SYNTHETIC COMPOUNDS FOR TREATMENT OF INFLAMMATION

(75) Inventors: Robert S. Jacobs, Santa Barbara, CA (US); Claudia E. Moya, Santa Barbara, CA (US); Amy E. Wright, Fort Pierce, FL (US)

(73) Assignees: The Regents of the University of California, Oakland, CA (US); Harbor Branch Oceanographic Inst., Fort Pierce, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/211,370

(22) Filed: Aug. 5, 2002

(65) Prior Publication Data

US 2003/0022815 A1 Jan. 30, 2003

Related U.S. Application Data

(63) Continuation-in-part of application No. 09/916,470, filed on Jul. 27, 2001, now Pat. No. 6,444,697, which is a continuation of application No. 09/349,316, filed on Jul. 8, 1999, now Pat. No. 6,323,233.
(60) Provisional application No. 60/091,991, filed on Jul. 8, 1998.

(51) Int. Cl.$^7$ ...................... A61K 31/40; A61K 31/405
(52) U.S. Cl. ...................... 514/408; 514/414; 514/415; 514/416; 514/417; 514/419
(58) Field of Search ................ 514/408, 414, 514/415, 416, 417, 419

(56) References Cited

U.S. PATENT DOCUMENTS

| 4,866,084 A | 9/1989 | Gunasekera et al. |
|---|---|---|
| 4,895,844 A | 1/1990 | Komoto et al. |
| 4,970,226 A | 11/1990 | Sun et al. |
| 5,290,777 A | 3/1994 | McConnell et al. |
| 5,464,835 A | 11/1995 | McConnell et al. |
| 5,955,462 A | 9/1999 | Jacobs et al. |
| 6,090,811 A | 7/2000 | Jacobs et al. |
| 6,291,501 B1 | 9/2001 | Wright et al. |
| 6,323,233 B1 | 11/2001 | Wright et al. |
| 6,444,697 B2 | 9/2002 | Wright et al. |

OTHER PUBLICATIONS

Amat–Guerri, et al. (1981) "The Formation of 1– and 3–Substituted Indoles in the Reaction between Indole and Sodium Glyoxylate" Chem. Letts. 4:511–541.

Earle, et al. (1991) "Bis–Trimethylsilylacetamide: A Reagent for the Control of Friedel–Crafts Alkylation Reactions Using Methyl Chloromethoxyacetate" Tetrahedron Letts. 32(43):6171–6174.

Hogan and Sainsbury (1984) "An Efficient Synthesis of Streptindole" Synthesis 10:872.

Wright (2000) "Marine Organisms as a Source of Novel Lead Structures for Drug Development" Biodiversity New Leads For The Pharmaceutical And Agrochemical Industries. Eds. Wrigley et al. Royal Society of Chemistry. pp. 113–125.

*Primary Examiner*—Theodore J. Criares
*Assistant Examiner*—Jennifer Kim
(74) *Attorney, Agent, or Firm*—Jacobson Holman PLLC

(57) ABSTRACT

Novel uses of biologically active bis-heterocyclic e.g. bis-indole alkaloid compounds which have improved activity are disclosed. Pharmaceutical compositions containing the compounds are also disclosed. Specifically, the novel utility pertains to the anti-immunogenic and neurogenic inflammatory properties exhibited by the bis-indole compounds and their analogs.

15 Claims, 2 Drawing Sheets

SYNTHETIC COMPOUNDS FOR TREATMENT OF INFLAMMATION

RELATED APPLICATION DATA

This application is a continuation-in-part of U.S. Ser. No. 09/916,470, filed Jul. 27, 2001, naming Amy E. Wright, Ralph-Heiko Mattem, and Robert S. Jacobs as inventors, now U.S. Pat. No. 6,444,697, which is a continuation of U.S. Ser. No. 09/349,316, filed Jul. 8, 1999, naming Amy E. Wright, Ralph-Heiko Mattem, and Robert S. Jacobs as inventors, now U.S. Pat. No. 6,323,233; which claims the benefit of U.S. Ser. No. 60/091,991, filed Jul. 8, 1998, naming Amy E. Wright, Ralph-Heiko Mattem, and Robert S. Jacobs as inventors, all of which are herein incorporated by reference in their entirety.

STATEMENT REGARDING FEDERALLY SPONSORED RESEARCH OR DEVELOPMENT

This invention was made with Government support under Grant No. NA06RG0142, awarded by the National Oceanic & Atmospheric Administration (NOAA). The Government has certain rights in this invention.

BACKGROUND OF THE INVENTION

1. Field of the Invention

The subject invention pertains to compounds that are useful as anti-inflammatory agents and to compositions containing such compounds as active ingredients. More particularly, the invention concerns novel uses for biologically active bis-heterocyclic compounds, e.g. bis-indoles, and to pharmaceutical compositions containing these compounds. The novel use of the compounds relates to the anti-inflammatory properties of the disclosed bis-heterocyclic compounds. Specifically exemplified herein are the compounds identified as Soritin B, bis-(1H-indol-3-yl)-acetic acid methyl ester, Soritin C, bis-2,2-(1-methyl-indol-3-yl) acetic acid methyl ester, Soritin D, bis-2,2-(1-methyl-indol-3-yl) acetic acid, and their salts, analogs, and derivatives.

2. Description of the Related Art

The prevention and control of inflammation is of prime importance to man, and much research has been devoted to development of compounds having anti-inflammatory properties. Certain methods and chemical compositions have been developed which aid in inhibiting or controlling inflammation, but additional anti-inflammatory methods and compositions are needed.

Bis-heterocyclic compounds, such as bis-indoles, have been previously described as having antimicrobial, antitumor or antiviral activity. See U.S. Pat. Nos. 5,955,462; 6,090,811; and 6,291,501, which are herein incorporated by reference. Specifically, the bis-indole compounds known as topsentins are disclosed in U.S. Pat. No. 4,866,084 and nortopsentins are disclosed in U.S. Pat. No. 4,970,226, which are herein incorporated by reference. Dragmacidin and its related compounds isolated from the marine sponge of the Dragmacidon sp. are disclosed in U.S. Pat. No. 4,895,844, which is herein incorporated by reference. These patents are herein incorporated by reference. These compounds as well as the homocarbonyl topsentins and hamacanthins have also been described as having inhibitory activity against cellular inflammatory responses. See U.S. Pat. Nos. 5,290,777 and 5,464,835, which are also hereby incorporated by reference. The present invention provides compounds having advantageous potent anti-inflammatory activity.

Other advantages and further scope of applicability of the present invention will become apparent from the detailed descriptions given herein; it should be understood, however that the detailed descriptions, while indicating preferred embodiments of the invention, are given by way of illustration only, since various changes and modifications within the spirit and scope of the invention will become apparent from such descriptions.

SUMMARY OF THE INVENTION

The present invention provides compounds that are useful as anti-inflammatory agents.

In one example, the compounds useful according to the subject invention have the following formula:

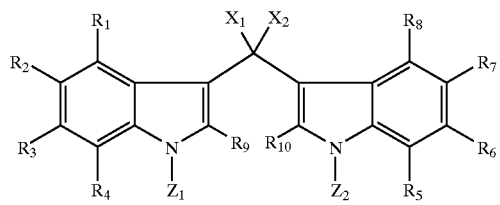

wherein $R_{1-10}$ are the same or different selected from —H, —OH, halogen, —COOH, —COOR, $C_1$–$C_8$ alkyl, $C_1$–$C_8$ alkoxyl, mesyl, tosyl, —OCOR, or $NZ_1Z_2$ (wherein the Zs can be the same or different);

$X_1$ and $X_2$ are the same or different selected from —H, —R, —COY, $C(NZ_1)Y$;

Y is —H, —OH, $NZ_1Z_2$ (wherein the $Z_1$, and $Z_2$ can be the same or different) $C_1$–$C_8$ alkyl, $C_1$–$C_8$ alkoxyl or an amino acid linked through the amine functionality forming an amide bond;

$Z_1$ and $Z_2$ are the same or different and independently selected from —H, —OH, $C_1$–$C_8$ alkyl, $C_1$–$C_8$ alkoxyl or —COR; and R is $C_1$–$C_8$ alkyl, or aryl.

Preferred embodiment of the subject invention pertain to the bis-indole compounds: Soritin A, bis-(1H-indol-3-yl)-acetic acid, HB-238, (I); bis(3,3'indolyl)methane, HB-236, (II); and 2,2-bis(3,3'indolyl) acetaldehyde, HB-237 (III) as follows:

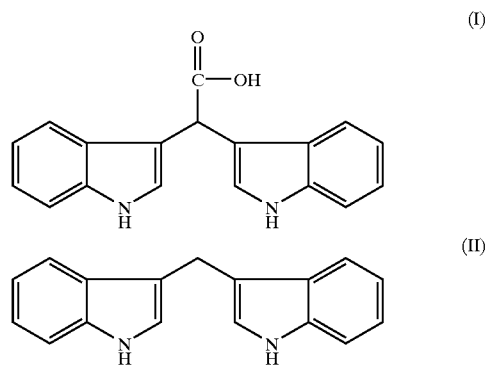

-continued (III)

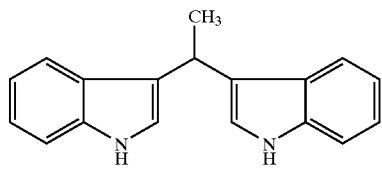

Another preferred embodiment of the present invention is Soritin B, bis-(1H-indol-3-yl)-acetic acid methyl ester, which has the following structural formula (IV):

(IV)

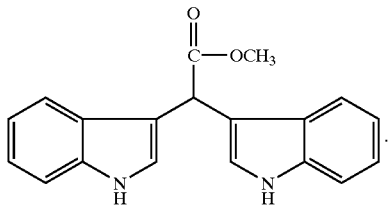

Yet another preferred embodiment of the present invention is Soritin C, bis-2,2-(1-methyl-indol-3-yl) acetic acid methyl ester, which has the following structural formula (V):

(V)

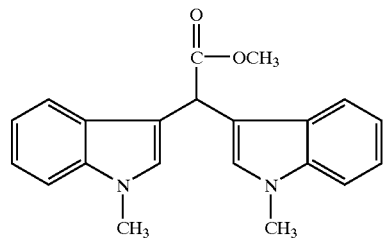

Yet still another preferred embodiment of the present invention is Soritin D, bis-2,2-(1-methyl-indol-3-yl) acetic acid, which has the following structural formula (VI):

(VI)

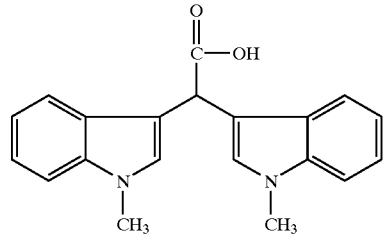

As described herein, the invention also comprises pharmaceutical compositions, e.g. anti-inflammatory compositions, containing as an active ingredient an effective amount, preferably between about 0.1% to about 45.0%, especially about 1.0% to about 25.0%, by weight based on the total weight of the composition, of one or more compounds according to the formula expressed above and a non-toxic, pharmaceutically acceptable carrier or diluent. In addition, a pharmaceutical composition can comprise at least one of the subject compounds and a second component comprising at least one other active compound. Such other active compounds include but are not limited to, anti-inflammatory compounds for example, steroidal compounds, including hydrocortisone and the like; or non-steroidal anti-inflammatory agents, including acetylsalicylic acid (aspirin), ibuprofen, acetaminophen, indomethacin, and the like. The second active ingredient can include antiviral, antibacterial, anti-fungal or other anti-microbial compounds or anti-tumor compounds as well.

As described herein, the invention further comprises processes for the production of compounds and compositions of the invention and novel methods of use thereof, e.g. methods of inhibition of the inflammatory response in an animal.

In accordance with the invention, methods for inhibiting inflammation comprise administering to an animal in need of such treatment an effective amount of the pharmaceutical composition.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DETAILED DESCRIPTION OF THE INVENTION

Figure 1:
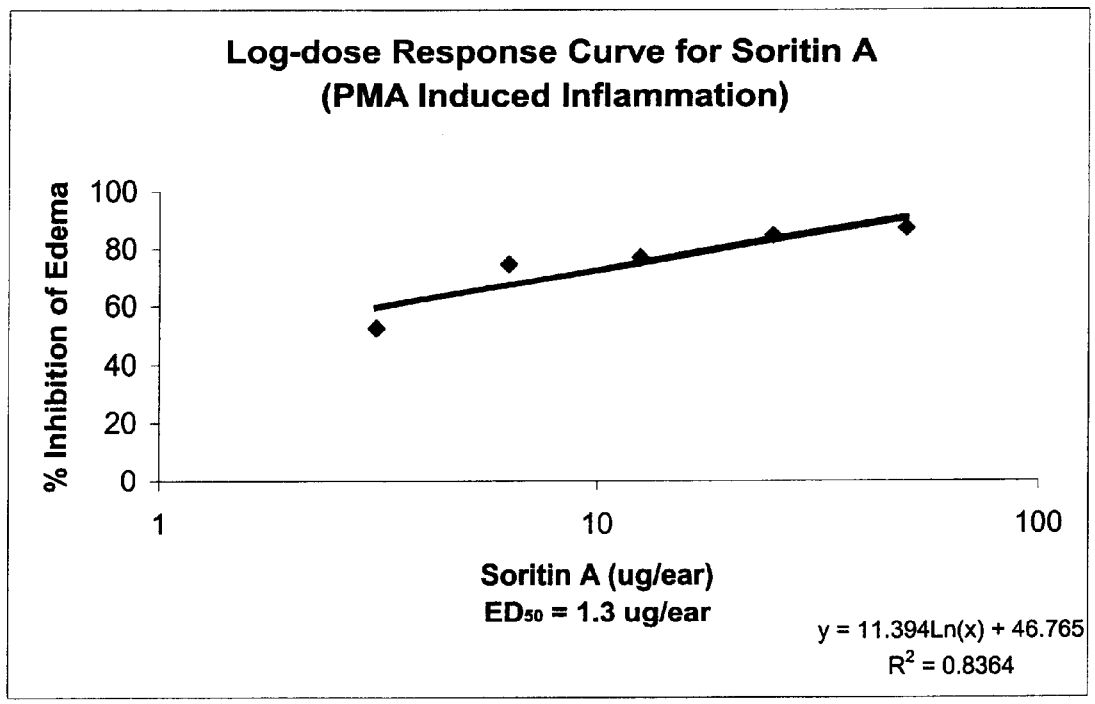
FIG. 1 shows the dose response for Soritin A (HB-238) as measured by percent inhibition of edema in the PMA-induced mouse ear anti-inflammatory assay.
Figure 2:
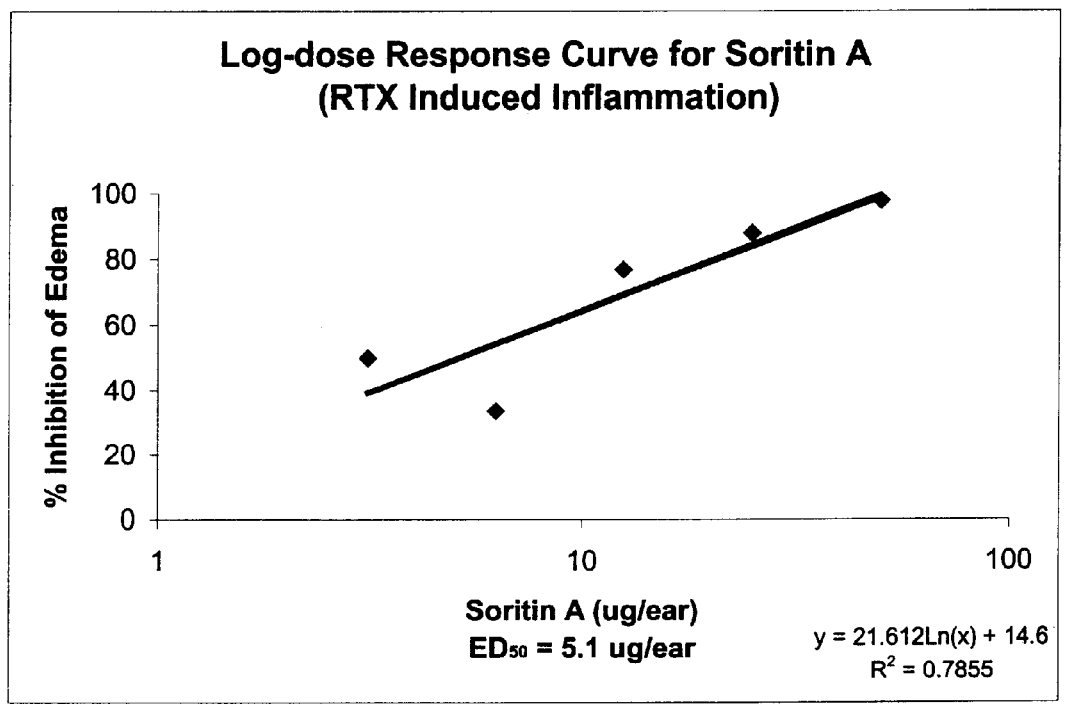
FIG. 2 shows the dose response for Soritin A (HB-238) as measured by percent inhibition of edema in the RTX-induced mouse ear anti-inflammatory assay.

The subject invention pertains to a novel use as an anti-inflammatory agent of bis-heterocyclic compounds and compositions comprising the bis-heterocyclic compounds. Surprisingly, the bis-heterocycle compounds of the subject invention can be highly effective in inhibiting immunogenic and neurogenic inflammation.

As provided herein, the Soritin compounds of the present invention have the following formula:

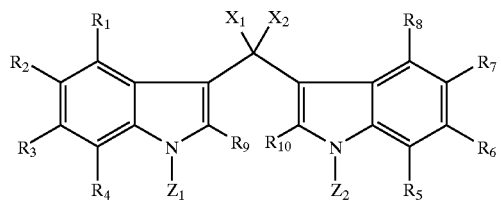

wherein $R_{1-10}$ are the same or different selected from —H, —OH, halogen, —COOH, —COOR, $C_1$–$C_8$ alkyl, $C_1$–$C_8$ alkoxyl, mesyl, tosyl, —OCOR, or $NZ_1Z_2$ (wherein the Zs can be the same or different);

$X_1$ and $X_2$ are the same or different selected from —H, —R, —COY, $C(NZ_1)Y$;

Y is —H, —OH, $NZ_1Z_2$ (wherein the $Z_1$ and $Z_2$ can be the same or different) $C_1$–$C_8$ alkyl, $C_1$–$C_8$ alkoxyl or an amino acid linked through the amine functionality forming an amide bond;

$Z_1$ and $Z_2$ are the same or different and independently selected from —H, —OH, $C_1$–$C_8$ alkyl, $C_1$–$C_8$ alkoxyl or —COR; and R is $C_1$–$C_8$ alkyl, or aryl.

A preferred embodiment of the subject invention pertains to the bis-indole compounds Soritin A, HB-238, (I), bis(3, 3'indolyl)methane, HB-236, (II) and 2,2-bis(3,3'indolyl) acetaldehyde, HB-237 (III).

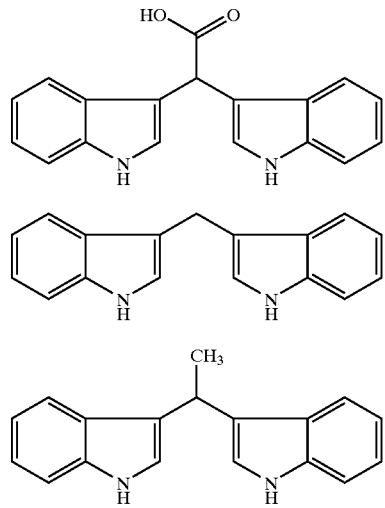

(I)

(II)

(III)

Other preferred embodiments of the present invention include Soritin B (IV), Soritin C (V), and Soritin D (VI).

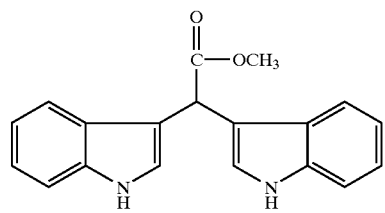

(IV)

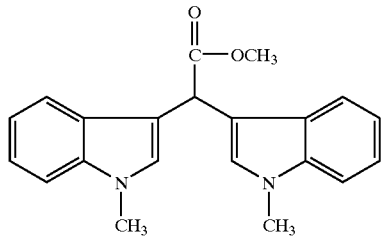

(V)

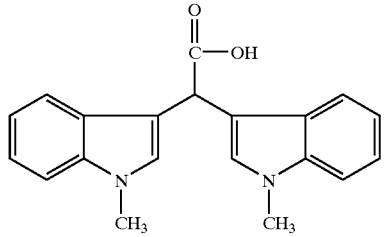

(VI)

Skilled chemists having the benefit of the instant disclosure can readily use standard synthetic procedures to prepare the subject compounds. A variety of coupling procedures can be used including dimerization of indoles with aldehydes, Friedel Craft acylations, Friedel Craft alkylations and various metal mediated coupling reactions. Preparation of amino acid substituted Soritin A can easily be conducted using standard peptide coupling reagents such as DCC, BOP, PyBOP, HBTU and TBTU.

The generalized procedure set for in Example 7 may be used to produce a variety of Soritin analogs such as those provided herein. Specifically, commercially available or readily synthesizable indoles may be reacted with glyoxylic acid, followed by esterification to yield Soritin B analogs (IV) as per Scheme I.

Scheme I
General Synthetic Scheme

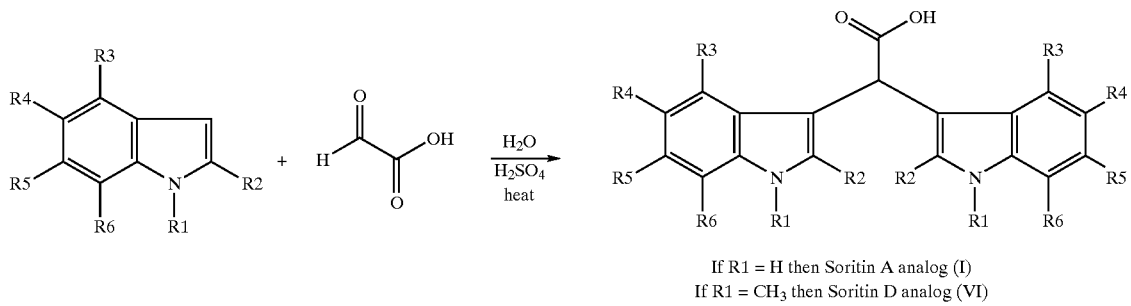

If R1 = H then Soritin A analog (I)
If R1 = CH$_3$ then Soritin D analog (VI)

R$_7$OH
H$_2$SO$_4$
heat

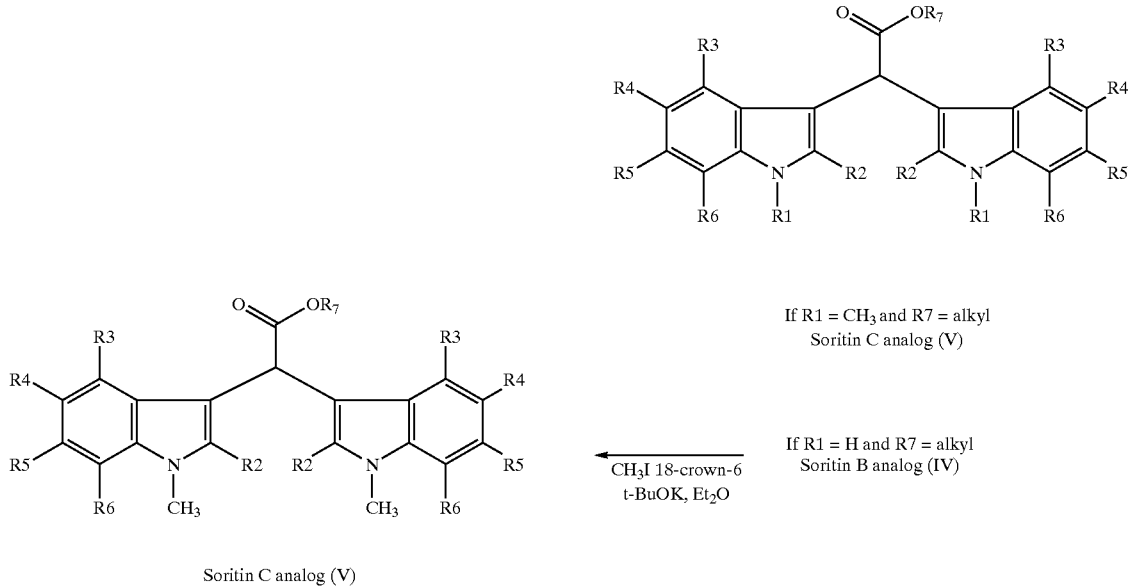

Soritin C analog (V)

Soritin C analogs (N-methyl Soritins) can be prepared by either beginning with an N-methyl indole or by treating either a Soritin A or Soritin B analog with methyl iodide in ether containing potassium t-butoxide and 18-crown-6 ether. Those skilled in the art can make modifications to this simple scheme to achieve the synthesis of the same compounds. For example the esterification procedure could be modified to remove water using a Starke apparatus to improve yields.

A novel use for the described compounds and compositions is their administration to an animal, e.g., a human, as an agent in the control of a neurogenic or immunogenic inflammatory response. The determination that the subject compounds have inhibitory activity against immunogenic and neurogenic inflammation is unexpected and advantageous.

Anti-inflammatory activity can occur by modes of action which can include, but are not limited to, lipid-mediated inflammatory responses, e.g. (i) suppression of cellular activation of phospholipase A2, either directly (as is known for the anti-inflammatory compound, manoalide) or indirectly (as is known for the anti-inflammatory compound, hydrocortisone); (ii) by inhibiting, or controlling, cyclooxygenation of arachidonic acid, similar to the action of non-steroidal anti-inflammatory drugs; or (iii) by affecting lipooxygenase products of peroxidase reactions to arachidonic acid, or by non-lipid-mediated inflammatory responses, e.g., protease-induced inflammatory responses, and the like.

The compounds and compositions of the subject invention advantageously can block the immunogenic inflammatory pathway, thereby providing a method for inhibiting immunogenic inflammation. Accordingly, the subject compounds and compositions can be useful in the treatment of neurogenic inflammation, present in different processes, such as diabetes, asthma, cystitis, gingivitis, migraine, dermatitis, rhinitis, psoriasis, inflammation of sciatic and lumbar nerves, gastrointestinal processes, ocular inflammation, and acute allergic response, asthma, rheumatoid arthritis, osteoarthritis and other inflammatory conditions involving acute and/or chronic joint inflammation in a subject, preferably mammalian, more preferably human.

Neurogenic inflammation is evoked by neuropeptides released from primary afferent nerve terminals and by other secondarily released inflammatory mediators. Specifically, neurogenic inflammation can be evoked by neuropeptides, such as substance P (SP), calcitonin gene-related peptide (CGRP), vasoactive intestinal peptide (VIP), and neurokinin A (NKA), released from primary afferent C-fiber nerve terminals and histamine, secondarily released from mast cells. See Dray, A. (1992) *Biochem. Pharm.* 44(4):611–15, which is herein incorporated by reference.

It is known that capsaicin (CAP), the active constituent found in cayenne pepper, induces an acute neurogenic inflammatory response when applied topically to skin. CAP is a highly selective pain producing substance that selectively stimulates nociceptive and thermal-sensitive nerve endings in tissues by acting on a specific membrane receptor. The mode of action of capsaicin therefore differs significantly from phorbol myristate acetate (PMA)-induced inflammation. By comparison, PMA elicits its pro-inflammatory effects through cellular activation of specific immune cells, such as macrophages and neutrophils. Consequently, the pain response to PMA develops more slowly than the immediate, but transient, pain response to capsaicin.

The compounds and compositions of the subject invention advantageously can block the nociceptive (CAP-induced) inflammatory pathway, thereby providing a method for inhibiting neurogenic inflammation. Accordingly, the subject compounds and compositions can be useful in the treatment of chronic pain, migraines, thermal-induced pain, such as sunburn, or other thermal and nociceptive pain, and chronic pain associated with arthritis. Uses can also include other inflammatory conditions that involve a neurogenic pain-producing component, e.g., certain metastic carcinomas or inflammation of the blood vessels.

For purposes of the subject invention, unless otherwise noted, the terms "inflammation" and "inflammatory response" refer to any and all such inflammatory reactions including, but not limited to, immune-related responses and/or allergic reactions to a physical, chemical, or biological stimulus. "Anti-neurogenic inflammatory activity," as used herein, will be understood by those of ordinary skill in the art to mean biological activity inhibiting or controlling a neurogenic inflammatory response.

The compounds of the subject invention can be used to treat a variety of skin conditions including, but not limited to, radiation irritation and burns (including UV and ionizing), chemical burns, rhinitis, thermal burns, and reddening of the skin, as well as neurogenic inflammation, present in different processes, such as diabetes, asthma, cystitis, gingivitis, migraine, dermatitis, psoriasis, inflammation of sciatic and lumbar nerves, gastrointestinal processes, ocular inflammation, and acute allergic response, poison oak, rheumatoid arthritis, osteoarthritis and other inflammatory conditions involving acute and/or chronic joint inflammation in a subject, preferably mammalian, more preferably human. The compounds of the subject invention can also be used to promote wound healing and prevent or inhibit pain.

The Soritin compounds of the present invention may be used in combination with or as a substitution for treatments of the above conditions. For example, the Soritin compounds may also be used alone or combination with an anti-neoplastic agent to treat cancer. The Soritin compounds of the invention may be used alone or in combination with glucocorticoids, cyclooxygenase (COX) inhibitors, aspirin, or methotrexate to treat inflammatory disorders such as rheumatoid arthritis. Further, the Soritin compounds of the present invention may be used alone or in combination with analgesics to treat, prevent or inhibit pain.

A Soritin compound of the present invention may be administered in a therapeutically effective amount to a mammal such as a human. A therapeutically effective amount may be readily determined by standard methods known in the art. As defined herein, a therapeutically effective amount of a compound of the invention ranges from about 1 to about 2400 mg/kg body weight, preferably about 10 to about 1000 mg/kg body weight, and more preferably about 10 to about 500 mg/kg body weight. Preferred topical concentrations include about 0.1% to about 10% in a formulated salve. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of the Soritin compound can include a single treatment or, preferably, can include a series of treatments.

In a preferred example, a subject is treated with a compound of the invention in the range of between about 1 to about 2400 mg/kg body weight, at least one time per week for between about 1 to about 24 weeks, and preferably between about 1 to about 10 weeks. It will also be appreciated that the effective dosage of the compound used for treatment may increase or decrease over the course of a particular treatment. Changes in dosage may result and become apparent by standard diagnostic assays known in the art. In some conditions chronic administration may be required.

Except insofar as any conventional media or agent is incompatible with the active compound, use thereof in the compositions is contemplated. Supplementary active compounds can also be incorporated into the compositions. Supplementary active compounds include glucocorticoids, cyclooxygenase (COX) inhibitors, aspirin, methotrexate, taxol, and the like.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The Soritin compounds of the present invention may be prepared using reaction routes, synthesis schemes and techniques available in the art using starting materials that are readily available. The following Examples are intended to illustrate but not to limit the invention. A more complete understanding of the invention can be obtained by reference to the following specific examples of compounds, compositions, and methods of the invention. It will be apparent to those skilled in the art that the examples involve use of materials and reagents that are commercially available from known sources, e.g., chemical supply houses, so no details are given respecting them. These Examples should not be construed as limiting. All percentages are by weight and all solvent mixture proportions are by volume unless otherwise noted.

EXAMPLE 1

Preparation of Soritin A, HB-238 (I)

One equivalent of indole was suspended in water and one equivalent of glyoxylic acid was added. The mixture was vigorously stirred at 85° C. for three hours during which a brown precipitate was formed. The precipitate was filtered and dissolved in aqueous NaOH solution (pH=12). Upon acidification (pH=2) with 5 N HCl, the product precipitated and was filtered and dried in vacuum. Yield: 84.5%

Characterization: pink crystals, mp: 182° C. (decomposition) $^1$H NMR ($\delta$ DMSO-$d_6$): 12.60 (brs, 1H), 10.96 (2H, s), 7.78 (2H, d, J=8.3), 7.54 (2H, d, J=8.3), 7.43 (2H, s), 7.22 (2H, t, J=7.4), 7.13 (t, 2H, J=7.4), 5.63 (1H,s) $^{13}$C NMR ($\delta$ DMSO-$d_6$): 174.9, 136.7, 126.9, 124.0, 121.4, 119.3, 118.8, 113.2, 111.8, 40.8.

EXAMPLE 2

Synthesis of Bis(3,3'indolyl)methane HB-236 (II)

Two equivalents of indole was suspended in water and one equivalent of formaldeyde (as formalin) was added. The mixture was vigorously stirred at 85° C. in the dark. After approximately 30 minutes, the product started to precipitate and the reaction mixture was stirred for another five hours. The product was filtered and recrystallized from methanol to yield white crystals. Yield: 79.3%

Characterization: white crystals, mp: 162° C., $^1$H NMR ($\delta$ DMSO-$d_6$): 10.71 (2H, s), 7.53 (2H, d, J=8.0), 7.32 (2H, d, J=8.0),7.14(2H, s), 7.04 (2H, t, J=7.2), 6.93 (t, 2H, J=7.2), 4.14 (2H, s) $^{13}$C NMR ($\delta$ DMSO-$d_6$): 136.4, 127.2, 122.7, 120.7, 118.6, 118.0, 114.2, 111.2, 20.9

EXAMPLE 3

Synthesis of 2,2-Bis(3,3'indolyl) acetaldehyde, HB-237 (III)

Two equivalents of indole was suspended in water and one equivalent of acetaldehyde dimethyl acetal was added. The mixture was vigorously stirred at 85° C. in the dark. The product started to precipitate and the reaction mixture was stirred for another five hours. The product was filtered and recrystallized from methanol. Yield: 59%

Characterization: yellowish crystals, mp: 172° C. $^1$H NMR ($\delta$ DMSO-$d_6$): 10.72 (2H, s), 7.47 (2H, d, J=8.3), 7.34 (2H, d, J=8.3), 7.15 (2H, s), 7.03 (2H, t, J=7.4), 6.89 (t, 2H, J=7.4), 4.61 (1H, q, J=7.4), 1.78 (3H. d. J=7.4) $^{13}$C NMR ($\delta$ DMSO-$d_6$): 136.8, 126.7, 121.7, 120.8, 120.3, 119.2, 118.0, 111.5, 28.0, 22.1.

EXAMPLE 4

Inhibition of PMA-Induced Inflammation (Edema) of the Mouse Ear

The test compound and a known inflammatory agent, phorbol myristate acetate (PMA), are topically applied simultaneously to the left ears of mice. Three hours and 20 minutes following application, the mice are sacrificed. Both left ears and right ears are removed and standard sized bores taken. Edema (inflammation) is measured as the difference in weight between left and right ears. See Van Arman, C. G. (1974) Clin. Pharmacol. Ther. 16:900–904, which is herein incorporated by reference.

Bis-heterocycle compounds of the subject invention, e.g., the bis-indole compounds, show significant anti-inflammatory properties. When screened for the ability to reduce edema in mouse ears caused by application of phorbol myristate acetate, Soritin A (I) was found to have greater potency than the known anti-inflammatories hydrocortisone, indomethacin, manoalide and topsentin. See Tables 1 and 2.

TABLE 1

Relative potency of Soritin A, (I), topsentin, manoalide, hydrocortisone and indomethacin in the topical inhibition of PMA-induced mouse ear edema

| Compound | $ED_{50}$ ($\mu$g/ear) |
|---|---|
| Hydrocortisone | 20 |
| Indomethacin | 250 |
| Manoalide | 100 |
| Topsentin | 15 |
| Soritin A (I) | 1.3 |

TABLE 2

| Treatment | Right ear (mg) | Left ear (mg) | Difference (mg) | Mean | Standard Dev. | SEM | % Inh. Of Edema |
|---|---|---|---|---|---|---|---|
| PMA | 10 | 23.2 | 13.2 | 13.7 | 0.6 | 0.3 | |
| Control | 9.5 | 22.8 | 13.32 | | | | |
| 2 $\mu$g/ear | 8.6 | 23.2 | 14.6 | | | | |
| | 10.1 | 23.6 | 13.5 | | | | |
| Compound I | 10.3 | 12.0 | 1.7 | 1.7 | 0.4 | 0.2 | 87.5 |
| 50 $\mu$g/ear | 10.2 | 11.8 | 1.6 | | | | |
| | 10.5 | 12.7 | 2.2 | | | | |
| | 10.0 | 11.3 | 1.3 | | | | |
| Compound I | 9.9 | 11.6 | 1.7 | 2.1 | 1.3 | 0.7 | 84.9 |
| 25 $\mu$g/ear | 9.9 | 13.3 | 3.4 | | | | |
| | 12.5 | 12.9 | 0.4 | | | | |
| | 9.5 | 12.7 | 2.8 | | | | |
| Compound I | 9.5 | 13.6 | 4.1 | 3.1 | 1.9 | 0.9 | 77.3 |
| 12.5 $\mu$g/ear | 8.8 | 10.7 | 1.9 | | | | |
| | 9.8 | 11.0 | 1.2 | | | | |
| | 9.7 | 14.9 | 5.2 | | | | |
| Compound I | 10.8 | 12.0 | 1.2 | 3.4 | 2.0 | 1.0 | 75.1 |
| 6.25 $\mu$g/ear | 8.5 | 13.0 | 4.5 | | | | |
| | 8.6 | 11.0 | 2.4 | | | | |
| | 9.9 | 15.4 | 5.5 | | | | |
| Compound I | 10.2 | 14.2 | 4.0 | 6.4 | 2.6 | 1.3 | 52.9 |
| 3.12 $\mu$g/ear | 9.0 | 17.7 | 8.7 | | | | |
| | 9.2 | 17.9 | 8.7 | | | | |
| | 8.6 | 12.9 | 4.3 | | | | |

EXAMPLE 5

Inhibition of Resiniferatoxin-Induced Inflammation (Edema) of the Mouse Ear

Induction of mouse ear edema can be conducted according to known methods. See Inoue, 1-f., N. Nagata, Y. Koshffiara (1993), which is herein incorporated by reference. Compounds to be tested for anti-neurogenic inflammatory activity are topically applied in acetone to the ears of mice in a solution that includes the edema-causing irritant resiniferatoxin (RTX). RTX alone (0.1 $\mu$g/ear) or in combination with various dilutions of test compound are applied to both sides of the left ears (5 mice per treatment group) and acetone is applied to all right ears. After a 30-minute incubation, the mice are sacrificed, the ears removed, and bores taken and weighed. Edema is measured by subtracting the weight of the right ear (acetone control) from the weight of the left ear (treated). Results are recorded as % decrease (inhibition) or % increase (potentiation) in edema relative to the control group edema.

Soritin A proved to be capable of reducing edema in mouse ears caused by application of resiniferatoxin (RTX). At a dose of 50 µg/ear of Soritin A (I), RTX-induced edema was inhibited by approximately 97.7%. The $ED_{50}$ for inhibition of RTX-induced edema was observed to be 5.1 µg/ear. See Table 3.

from the testing that the compounds of the invention are effective for anti-inflammatory uses.

Therapeutic application of the new compounds and compositions containing them can be contemplated to be accomplished by any suitable therapeutic method and technique presently or prospectively known to those skilled in the art. Further the compounds of the invention have use as starting material for intermediates for the preparation of other useful compounds and compositions.

In one preferred embodiment, the compounds or compositions of the subject invention are administered in a lotion

TABLE 3

| Treatment | Right ear (mg) | Left ear (mg) | Difference (mg) | Mean | Standard Dev. | SEM | % Inh. Of Edema |
|---|---|---|---|---|---|---|---|
| RTX | 10.2 | 20.2 | 10.0 | 12.0 | 2.2 | 1.0 | |
| Control | 10.5 | 23.7 | 13.2 | | | | |
| 0.1 µg/ear | 10.3 | 24.4 | 14.1 | | | | |
| | 10.9 | 24.4 | 13.5 | | | | |
| | 11.2 | 20.5 | 9.3 | | | | |
| Compound I | 10.9 | 11.0 | 0.1 | 0.3 | 0.8 | 0.4 | 97.7 |
| 50 µg/ear | 10.9 | 10.7 | −0.2 | | | | |
| | 11.4 | 11.2 | −0.2 | | | | |
| | 9.9 | 11.4 | 1.5 | | | | |
| Compound I | 9.9 | 14.0 | 4.1 | 1.5 | 1.7 | 0.7 | 87.9 |
| 25 µg/ear | 9.7 | 9.9 | 0.2 | | | | |
| | 10.0 | 12.1 | 2.1 | | | | |
| | 11.7 | 12.3 | 0.6 | | | | |
| | 10.6 | 10.9 | 0.3 | | | | |
| Compound I | 12.1 | 15.9 | 3.8 | 2.8 | 1.1 | 0.5 | 76.8 |
| 12.5 µg/ear | 10.6 | 14.2 | 3.6 | | | | |
| | 10.7 | 13.8 | 3.1 | | | | |
| | 10.7 | 11.8 | 1.1 | | | | |
| | 10.9 | 12.6 | 1.7 | | | | |
| | 11.1 | 14.5 | 3.4 | | | | |
| Compound I | 11.2 | 17.2 | 6.0 | 8.0 | 2.4 | 1.0 | 33.6 |
| 6.25 µg/ear | 11.9 | 23.1 | 11.2 | | | | |
| | 11.8 | 19.1 | 7.3 | | | | |
| | 10.6 | 20.7 | 10.1 | | | | |
| | 12.6 | 20.9 | 8.3 | | | | |
| | 11.8 | 16.8 | 5.0 | | | | |
| Compound I | 12.2 | 18.2 | 6.0 | 6.0 | 1.0 | 0.4 | 49.9 |
| 3.12 µg/ear | 10.8 | 16.8 | 6.0 | | | | |
| | 10.6 | 17.2 | 6.6 | | | | |
| | 12.6 | 19.7 | 7.1 | | | | |
| | 12.0 | 16.1 | 4.1 | | | | |
| | 11.8 | 18.1 | 6.3 | | | | |

In addition, the bis-indole compounds Bis(3,3'indolyl) methane (II) and 2,2-Bis(3,3indolyl) acetaldehyde (III) were tested for percent inhibition of RTX-induced edema. These compounds also show activity in this assay. See Table 4.

TABLE 4

Percent inhibition of RTX-induced edema in mouse ears by Soritin A and analogs

| | Compound Name | Dose | % Inhibition of Edema |
|---|---|---|---|
| Soritin A | HB-238 | 50 µg/ear | 97.7 |
| Bis(3,3'indolyl)methane | HB-236 | 50 µg/ear | 59.1 |
| Bis(3,3'indolyl)acetaldehyde | HB-237 | 50 µg/ear | 50.1 |

EXAMPLE 6

Formulation and Administration

The compounds of the invention are useful for various non-therapeutic and therapeutic purposes. It is apparent or other cosmetic preparation. This administration is done directly to the skin where anti-inflammatory activity is desired.

The dosage administration to a host in the above indications will be dependent upon the identity of the condition to be treated, the type of host involved, its age, weight, health, kind of concurrent treatment, if any, frequency of treatment, and therapeutic ration.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

Typically, the compositions of the subject invention will be formulated and packaged in a manner particularly adapted for use as an anti-inflammatory agent. Thus, such compositions would typically be accompanied with labeling or other literature describing the use of the composition as an anti-inflammatory agent.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the bis-heterocycle compounds, e.g., a bis-indole, as a first active ingredient plus a second active ingredient comprising an anti-inflammatory compound known in the art. Such known anti-inflammatory drugs include, but are not limited to, the steroidal anti-inflammatory drugs and the non-steroidal anti-inflammatory drugs (NSAIDs).

In accordance with this invention, pharmaceutically effective amounts of a known anti-inflammatory agent and the bis-heterocycle compounds are administered sequentially or concurrently to the patient. The most effective mode of administration and dosage regimen of bis-heterocycle compounds and anti-inflammatory agent will depend upon the type of condition to be treated, the severity and course of that condition, previous therapy, the patient's health status, and response to bis-indoles and the judgment of the treating physician. Bis-heterocycle compositions may be administered to the patient at one time or over a series of treatments.

Preferably, the bis-heterocycle, e.g., a bis-indole composition, and any second anti-inflammatory agent are administered sequentially to the patient, with the anti-inflammatory agent being administered before, after, or both before and after treatment with the bis-indole compound. Sequential administration involves treatment with the anti-inflammatory agent at least on the same day (within 24 hours) of treatment with bis-indole and may involve continued treatment with the anti-inflammatory agent on days that the bis-indole is not administered. Conventional modes of administration and standard dosage regimens of anti-inflammatory agents may be used. See Gilman, A. G. et al. eds. THE PHARMACOLOGICAL BASIS OF THERAPEUTICS, pp.697–713, 1482, 1489–1491 (1980); PHYSICIANS DESK REFERENCE, 1985 Edition, which is herein incorporated by reference. For example, indomethacin can be administered orally at a dosage of about 25–50 mg, three times a day. Higher doses can also be used. Alternatively, aspirin (about 1500–2000 mg/day), ibuprofen (about 1200–3200 mg/day), or conventional therapeutic doses of other anti-inflammatory agents can be used. Dosages of anti-inflammatory agents can be titrated to the individual patient.

According to one embodiment of this invention, the patient may receive concurrent treatments with the anti-inflammatory agents and compositions comprising bis-heterocycles, e.g. bis-indoles. For example, local intralesional, or intravenous injection of bis-indoles is preferred. See Gilman et al. supra at pp. 1290–91. The anti-inflammatory agent should preferably be administered by subcutaneous injection, subcutaneous slow release implant, or orally.

Alternatively, the patient can receive a composition comprising a combination of one or more bis-indole compounds and an anti-inflammatory agent according to conventional modes of administration of agents which exhibit antibacterial, anticancer, antitumor or anti-inflammatory activity. These include, for example, parenteral, subcutaneous, intravenous, or intralesional routes of administration.

The compounds used in these therapies can also be in a variety of forms. These include for example, solid, semi-solid and liquid dosage forms, such as tablets, pills, powders, liquid solutions or suspensions, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch and equivalent carriers and diluents. While effective amounts may vary, as conditions in which compositions are used vary, a minimal dosage required for anti-inflammatory activity is generally between 0.01 and 100 $\mu$g of the compound. To provide for the administration of such dosages for the desired therapeutic treatment, new pharmaceutical compositions of the invention will advantageously comprise between about 0.1% and 45%, and especially between about 1 and 15% by weight of the total of one or more of the new compounds based on the weight of the total composition including carrier or diluent.

Illustratively, dosage levels of the administered active ingredients can be: intravenous, 0.01 to about 50 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 50 mg/kg; and aerosol, 0.01 to about 50 mg/kg of animal (body) weight.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

EXAMPLE 7

Synthesis of Soritin Analogs

Soritin A analogs (I) synthesis of bisindole acetic acid derivatives may be prepared by dissolving or suspending 0.1 mol of indole derivative in 500 ml of distilled water in a 1000 ml round bottom flask fitted with a reflux condenser then adding 0.1 mol of glyoxylic acid (50% solution in water, Aldrich). The flask is then covered to protect from light. The reaction mixture should be stirred and then slowly heated to 50° C. using an oil bath. Once 50° C. is reached, 20 ml of 1M $H_2SO_4$ should then be added to the reaction mixture. The reaction mixture is heated to about 85° C. and allowed to proceed to completion. Most reactions are complete within 3 hours. The reaction progress can be monitored by TLC or HPLC. Dependent upon the product, it can either be purified by filtration followed by washing with cold water or purified by extraction with organic solvents such as ethyl acetate or chloroform.

Soritin B analogs (IV) may be synthesized by dissolving the appropriate product above in an alcohol (methanol, ethanol, propanol, or the like) in a round bottom flask fitted with a reflux condenser and protected from light. Six (6) drops of concentrated $H_2SO_4$ are added to the reaction mixture and it is heated to reflux for about 8 hours. The reaction progress can be monitored by TLC or HPLC. Once the reaction is judged complete, the solvent is reduced in volume by about two-thirds (⅔) by distillation under reduced pressure. Saturated aqueous NaCl solution is added. The aqueous solution is extracted three times with ethyl acetate. The combined ethyl acetate extracts are then washed 3 times with saturated sodium bicarbonate solution and then dried over magnesium sulfate. The dried ethyl acetate solution is filtered and then treated with activated carbon 100 mesh to remove any colored impurities. The filtrate is then concentrated by distillation under reduced pressure to yield the Soritin B analog.

EXAMPLE 8

Synthesis of Soritin B

One-tenth (0.1) mol of indole was suspended in 500 ml of distilled water in a 1000 ml round bottom flask fitted with a reflux condenser. One-tenth (0.1) mol of glyoxylic acid (50% solution in water, Aldrich) was added to the flask. The flask was covered with foil to protect the reaction products from light. The reaction mixture was stirred and slowly heated to 50° C. using an oil bath. Once 50° C. was reached, 20 ml of 1M $H_2SO_4$ was added to the reaction mixture. The reaction mixture was heated to about 85° C. (to melt the indole) and the reaction allowed to proceed to completion (>95% conversion of indole to Soritin A). Typically, the reaction is complete within 2 hours. The reaction progress can be monitored by TLC using silica gel plates eluted with heptane-ethyl acetate 3:1 (v/v). Compounds can be visualized either by charring after treatment with 2% vanillin in $H_2SO_4$, or by UV absorbance. The product precipitates from solution as a light pink solid. The product was removed by filtration and then washed with cold distilled water to yield substantially pure Soritin A. The product was freeze-dried for 24 hours to remove water. The final yield was 0.06 mol of Soritin A.

The freeze dried Soritin A was then dissolved in 500 ml of dry methanol in a round bottom flask fitted with a reflux condenser and protected from light. Six (6) drops of concentrated $H_2SO_4$ were added to the reaction mixture which was heated to reflux for about 6 hours. The reaction progress was monitored by TLC using silica gel plates eluted with heptane-ethyl acetate 3:1 (v/v). Compounds were visualized either by charring after treatment with 2% vanillin in $H_2SO_4$, or by UV absorbance. Once the reaction was judged complete (typical conversion after 6 hours is about 60%), the solvent was reduced in volume by about two-thirds (⅔) by distillation under reduced pressure. Saturated aqueous NaCl solution (500 ml) was added. The aqueous solution was extracted three times with ethyl acetate (200 ml portions). The combined ethyl acetate extracts were then washed two times with saturated sodium bicarbonate solution (100 ml) and then dried over magnesium sulfate. The dried ethyl acetate solution was filtered to remove the $MgSO_4$, and then treated with activated carbon (100 mesh) to remove colored impurities. The filtrate was then concentrated by distillation under reduced pressure to yield the crude reaction product. To remove unreacted starting material and indole formed by decomposition of Soritin A, the material was chromatographed over silica gel using a step gradient of ethyl acetate in heptane. Fractions are monitored by TLC as above. Fractions which were substantially pure Soritin B were combined to give an isolated yield of 0.025 mol of Soritin B.

NMR data for Soritin B: $^1$H NMR ($CDCL_3$, 500 MHz): δ8.01 (2H bs H-1), 7.56 (2H d, J=7.8 H-4), 7.20 (2H d, J=7.9 H-7), 7.11 (2H t, J=7.6 H-6), 7.03 (2H t, J=7.6 H-5), 6.88 (2H s, H-2), 5.45 (s H-1'), 3.67 (3H s, $OCH_3$) $^{13}$C NMR (CDCL3, 125 MHz): δ174.1 (s, C-2'), 136.5 (2C, s, C-7a'), 126.6 (2C, s, C-3a'), 123.4 (2C, d, C-2), 122.0 (2C, d, C-6), 119.5 (2C, d, C-5), 119.1 (2C, d, C-4), 113.3 (2C, s, C-3),111.3 (2C, d, C-7), 52.2 (q, $OCH_3$), 40.4 (d, C-1').

EXAMPLE 9

Soritin B Assay

The following assay was conducted to determine whether Soritin B had coloration in solution and when applied to skin and whether Soritin B exhibited anti-inflammatory properties.

Soritin B was dissolved in acetone and exhibited a light amber color. Soritin B in acetone alone and in combination with phorbol myristate acetate or resiniferatoxin did not exhibit any discernable coloration on test ears from the beginning to the end of the experiments provided herein. Thus, there was no coloration due to application of Soritin B. Additionally, overnight exposure to Soritin B did not result in any discernable redness or swelling at 50 μg/ear when compared to controls.

A. Inhibition of PMA-Induced Inflammation (Edema) of the Mouse Ear

Soritin B and a known inflammatory agent, phorbol myristate acetate (PMA), were topically applied simultaneously to the left ears of mice. Three hours and 20 minutes following application, the mice were sacrificed. Both left ears and right ears were removed and standard sized bores taken. Edema (inflammation) was measured as the difference in weight between left and right ears. See Van Arman, C. G. (1974) *Clin. Pharmacol. Ther.* 16:900–904, which is herein incorporated by reference.

Figure 3:
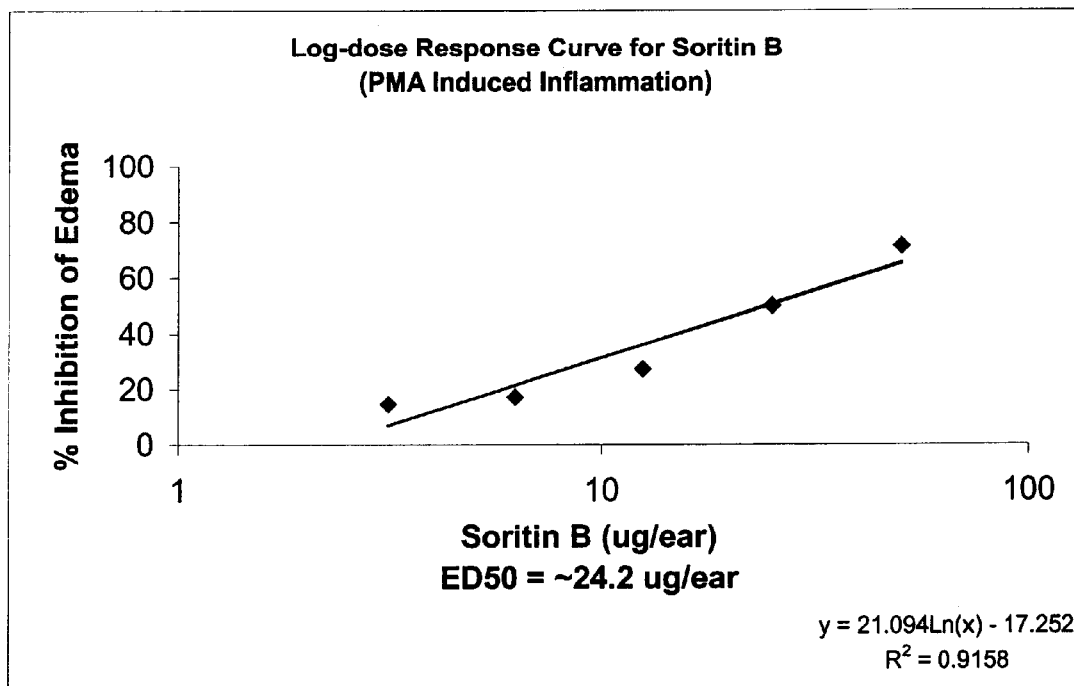
FIG. 3 shows the dose response for Soritin B as measured by percent inhibition of edema in the PMA-induced mouse ear anti-inflammatory assay.

Soritin B proved to be capable of reducing edema in mouse ears caused by application of phorbol myristate acetate (PMA). At a dose of 50 μg/ear of Soritin B, PMA-induced edema was inhibited by about 71.3%. The $ED_{50}$ for inhibition of PMA-induced edema was observed to be 24.2 μg/ear. See Table 5 and FIG. 3.

TABLE 5

| Treatment | Mean | SEM | % Inh. Of Edema |
|---|---|---|---|
| PMA Control 2.0 μg/ear n = 15 | 11.8 | 0.6 | |
| Soritin B 50 μg/ear n = 15 | 3.4* | 0.5 | 71.3 |
| Soritin B 25 μg/ear n = 15 | 5.9* | 0.7 | 50.0 |
| Soritin B 12.5 μg/ear n = 15 | 8.6* | 0.7 | 27.1 |
| Soritin B 6.25 μg/ear n = 15 | 9.7** | 0.5 | 17.1 |

TABLE 5-continued

| Treatment | Mean | SEM | % Inh. Of Edema |
|---|---|---|---|
| Soritin B 3.12 μg/ear n = 15 | 10.0** | 0.4 | 14.6 |

*Statistically significant difference between control and experimental group (T-test, p < 0.01)
**Statistically significant difference between control and experimental group (T-test, p < 0.05)

B. Inhibition of Resiniferatoxin-Induced Inflammation (Edema) of the Mouse Ear

Soritin B was tested for anti-neurogenic inflammatory activity by topically applying in acetone to the ears of mice in a solution that includes the edema-causing irritant resiniferatoxin (RTX) as provided above. See Inoue, 1-f., N. Nagata, Y. Koshffiara (1993), which is herein incorporated by reference. Specifically, RTX alone (0.1 μg/ear) or in combination with various dilutions of Soritin B was applied to both sides of the left ears (5 mice per treatment group) and acetone was applied to all right ears. After a 30-minute incubation, the mice are sacrificed, the ears removed, and bores taken and weighed. Edema was measured by subtracting the weight of the right ear (acetone control) from the weight of the left ear (treated). Results were recorded as % decrease (inhibition) or % increase (potentiation) in edema relative to the control group edema.

Figure 4:
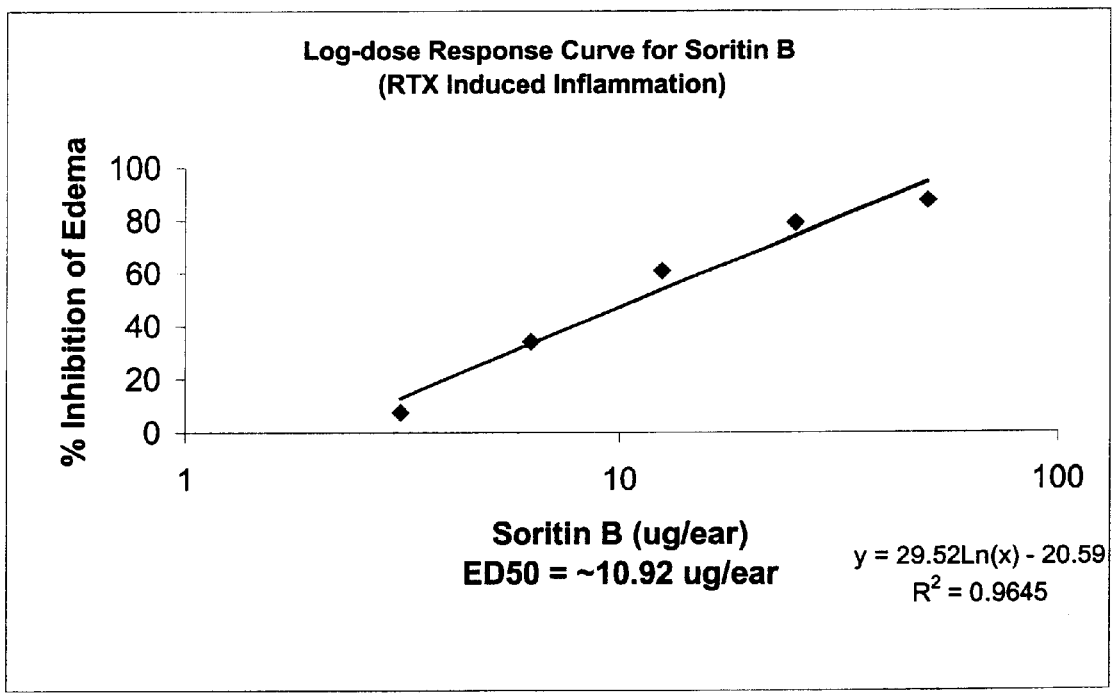
FIG. 4 shows the dose response for Soritin B as measured by percent inhibition of edema in the RTX-induced mouse ear anti-inflammatory assay.

Soritin B proved to be capable of reducing edema in mouse ears caused by application of resiniferatoxin (RTX). At a dose of 50 μg/ear of Soritin B, RTX-induced edema was inhibited by about 87.6%. The $ED_{50}$ for inhibition of RTX-induced edema was observed to be 10.9 μg/ear. See Table 6 and FIG. 4.

TABLE 6

| Treatment | Mean | SEM | % Inh. Of Edema |
|---|---|---|---|
| RTX Control 0.1 μg/ear n = 15 | 8.3 | 0.4 | |
| Soritin B 50 μg/ear n = 15 | 1.0* | 0.2 | 87.6 |
| Soritin B 25 μg/ear n = 14 | 1.7* | 0.3 | 79.2 |
| Soritin B 12.5 μg/ear n = 15 | 3.2* | 0.4 | 61.0 |
| Soritin B 6.25 μg/ear n = 15 | 6.5* | 0.5 | 34.3 |
| Soritin B 3.12 μg/ear n = 15 | 9.1 | 1.0 | 7.7 |

*Statistically significant difference between control and experimental group (T-test, p < 0.01)

EXAMPLE 10

Synthesis of Soritin C

One-tenth (0.1) mol of N-methylindole was suspended in 500 ml of distilled water in a 1000 ml round bottom flask fitted with a reflux condenser. One-tenth (0.1) mol of glyoxylic acid (50% solution in water, Aldrich) was added to the flask. The flask was covered with foil to protect the reaction products from light. The reaction mixture was stirred and slowly heated to 50° C. using an oil bath. Once 50° C. was reached, 20 ml of 1M $H_2SO_4$ was added to the reaction mixture. The reaction mixture was heated to about 80° C. and the reaction allowed to proceed to completion (>95% conversion of N-methyl indole to Soritin D). Typically the reaction is complete within 2 hours. The reaction progress can be monitored by TLC using silica gel plates eluted with heptane-ethyl acetate 3:1 (v/v). Compounds can be visualized either by charring after treatment with 2% vanillin in $H_2SO_4$, or by UV absorbance. The product precipitates from solution as a light tan solid. The product was removed by filtration and then washed with cold distilled water to yield substantially pure Soritin D. The product was freeze-dried for 24 hours to remove water. The final yield was 0.05 mol of Soritin D (VI).

The freeze dried Soritin D was then dissolved in 500 ml of dry methanol in a round bottom flask fitted with a reflux condenser and protected from light. Six (6) drops of concentrated $H_2SO_4$ were added to the reaction mixture which was heated to reflux for about 6 hours. The reaction progress was monitored by TLC using silica gel plates eluted with heptane-ethyl acetate 3:1 (v/v). Compounds were visualized either by charring after treatment with 2% vanillin in $H_2SO_4$, or by Uv absorbance. Once the reaction was judged complete (typical conversion after 6 hours is about 60%), the solvent was reduced in volume by about two-thirds (⅔) by distillation under reduced pressure. Saturated aqueous NaCl solution (500 ml) was added. The aqueous solution was extracted three times with ethyl acetate (200 ml portions). The combined ethyl acetate extracts were then washed two times with saturated sodium bicarbonate solution (100 ml) and then dried over magnesium sulfate. The dried ethyl acetate solution was filtered to remove the $MgSO_4$, and then treated with activated carbon (100 mesh) to remove colored impurities. The filtrate is then concentrated by distillation under reduced pressure to yield the crude reaction product. To remove unreacted starting material, material was chromatographed over silica gel using a step gradient of ethyl acetate in heptane. Fractions were monitored by TLC as above. Fractions which were substantially pure Soritin C were combined.

NMR data for Soritin C: $^1H$ NMR ($d_6$-DMSO, 500 MHz): δ7.56 (2H d, J=7.8 H-4), 7.38 (2H d, J=7.8 H-7), 7.22 (2H s, H-2), 7.15 (2H t, J=7.6 H-6), 7.01 (2H t, J=7.6, H-5), 5.49 (s H-1'), 3.71 (6H s, N-$CH_3$). 3.65 (3H, $OCH_3$) $^{13}C$ NMR (CDCL3, 125 MHz): δ173.15 (s, C-2'), 136.6 (2C, s, C-7a'), 128.0 (2C, s, C-2'), 126.6 (2C, s, C-3a), 121.2 (2C, d, C-6), 118.8 (2C, d, C-5 or C-4), 118.8 (2C, d, C-4 or C-5), 111.4 (2C, s, C3), 109.7 (2C, d, C-7), 51.8 (q, $OCH_3$), 39.6 (d, C-1'), 32.3 (q, 6H, N-$CH_3$).

To the extent necessary to understand or complete the disclosure of the present invention, all publications, patents, and patent applications mentioned herein are expressly incorporated by reference therein to the same extent as though each were individually so incorporated.

It should be understood that the examples and embodiments described herein are of illustrative purposes only and that various modification or changes in light thereof will be suggested to persons skilled in the art and are to be included within the spirit and purview of this application and the scope of the appended claims.

What is claimed is:

1. A method of treating, preventing, or inhibiting inflammation or a condition associated with inflammation in a subject in need thereof which comprises administering to the subject an effective amount of at least one Soritin compound selected from the group consisting of Soritin B, Soritin C, and Soritin D.

2. The method of claim 1, wherein the Soritin compound is Soritin B.

3. The method of claim 1, wherein the Soritin compound is Soritin C.

4. The method of claim 1, wherein the Soritin compound is Soritin D.

5. The method of claim 1, wherein the inflammation is neurogenic inflammation.

6. The method of claim 1, wherein the inflammation is inflammation of sciatic or lumbar nerves, ocular inflammation, or acute or chronic joint inflammation.

7. The method of claim 1, wherein the condition associated with inflammation is radiation or chemical irritation, rhinitis, a thermal burn, reddening of the skin, diabetes, asthma, cystitis, gingivitis, migraine, dermatitis, psoriasis, acute allergic response, rheumatoid arthritis, or osteoarthritis.

8. The method of claim 1, wherein the inflammation is the result of exposure to radiation, heat, chemicals, or poison oak.

9. The method of claim 1, wherein the subject is mammalian.

10. The method of claim 1, wherein the subject is human.

11. The method of claim 1, wherein the Soritin compound is administered in the form of a pharmaceutical composition.

12. The method of claim 1, further comprising administering a second Soritin compound.

13. The method of claim 1, further comprising administering at least one supplementary active compound selected from the group consisting of antibiotics, analgesics, and anti-inflammatory agents.

14. The method of claim 1, wherein the Soritin compound is administered in the form of a cosmetic composition.

15. The method of claim 1, wherein the Soritin compound lacks a discernable color and is non-staining when applied to the skin of the subject.

* * * * *